United States Patent [19]
Frisbee et al.

[11] Patent Number: 6,013,280
[45] Date of Patent: Jan. 11, 2000

[54] IMMEDIATE RELEASE DOSAGE FORMS CONTAINING MICROSPHERES

[75] Inventors: Steven E. Frisbee, Reston; Deirdre M. Barrow, Fairfax; Joseph Cascone, Chantilly; Barry D. McCarthy, Centreville; Bernard M. Kiernan, Ashburn; Hanan S. Anwar, Reston, all of Va.

[73] Assignee: Fuisz Technologies Ltd., Chantilly, Va.

[21] Appl. No.: 08/946,070

[22] Filed: Oct. 7, 1997

[51] Int. Cl.⁷ ........................................................ A61K 9/14
[52] U.S. Cl. ........................ 424/464; 424/489; 424/490; 424/497; 424/451; 514/951
[58] Field of Search ...................... 424/400, 451, 424/452, 464, 465, 470, 489, 490, 493; 514/951

[56] References Cited

U.S. PATENT DOCUMENTS

| | | | |
|---|---|---|---|
| 4,727,109 | 2/1988 | Schmidt et al. | 424/455 |
| 4,944,949 | 7/1990 | Story et al. | 424/451 |
| 5,139,740 | 8/1992 | Uesugi et al. | |
| 5,173,304 | 12/1992 | Lohner et al. | |
| 5,281,420 | 1/1994 | Kelm et al. | 424/452 |
| 5,292,461 | 3/1994 | Juch et al. | 264/37 |
| 5,445,769 | 8/1995 | Rutkowski et al. | 264/8 |
| 5,456,923 | 10/1995 | Nakamichi et al. | 424/489 |
| 5,458,823 | 10/1995 | Perkins et al. | 264/8 |
| 5,501,858 | 3/1996 | Fuisz | |
| 5,525,355 | 6/1996 | Brown et al. | 424/456 |
| 5,547,683 | 8/1996 | Yano et al. | |
| 5,683,720 | 11/1997 | Myers et al. | |

FOREIGN PATENT DOCUMENTS

| | | |
|---|---|---|
| 0 317 780 A1 | 5/1989 | European Pat. Off. ....... A61K 31/44 |
| 0 349 509 | 1/1990 | European Pat. Off. |
| 0 413 171 | 2/1991 | European Pat. Off. |
| 0 709 086 | 5/1996 | European Pat. Off. |
| 1 388 786 | 3/1975 | United Kingdom. |
| 93 25190 | 12/1993 | WIPO. |
| 97 02017 | 1/1997 | WIPO. |
| 97/02017 | 1/1997 | WIPO .............................. A61K 9/14 |
| 97 08950 | 3/1997 | WIPO. |

OTHER PUBLICATIONS

Hawley, A.R. et al. "Physical and chemical characterization of thermosoftened bases for molten filled hard gelatin capsule formulations" Drug Dev. Ind. Pharm. (1992), 18(16), pp. 1719–1739.

Mura, P. et al. "solid dispersions of ibuprofen in urea. Effects of urea on dissolution", Farmaco, ED. Prat. (1986) 41(12), pp. 377–387.

Taneja, L.N. et al.: "Solid dispersions of ketoprofen. In vitro characterization and bioavailability assessment" Indian Drugs (1997), 34(2), 72–77.

Smith, A. et al.: "The filling of molten ibuprofen into hard gelatin capsules", Int. J. Pharm. (1990), 59(2), pp. 115–119.

Halstenberg, Dr. Mechthild, "Medicines from the Extruder: A milestone in drug manufacturing technology at BASF Pharma", BASF Pharma Press Release (Sep. 6, 1994), pp. 1–4.

Grunhagen, Dr. Hans–Heinrich, "Melt Extrusion", BASF Pharma Press Release (Sep. 6, 1994), pp. 1–7.

Physician's Desk Reference for Non–Prescription Drugs, 16th ed. (1995), p. 870.

Primary Examiner—Thurman K. Page
Assistant Examiner—Brian K. Seidleck
Attorney, Agent, or Firm—Sandra Nolan; Richard D. Schmidt

[57] ABSTRACT

The invention deals with microspheres which are useful in pharmaceutical dosage forms. The microspheres contain active agents and solubilizing agents which have been processed via liquiflash techniques.

20 Claims, No Drawings

IMMEDIATE RELEASE DOSAGE FORMS CONTAINING MICROSPHERES

FIELD OF THE INVENTION

The invention deals with immediate, or fast, release dosage units for active agents which are not readily water soluble. The fast release of these active agents from pharmaceutical dosage forms is assured by delivering them via microspheres made using "liquiflash" techniques. Ibuprofen is representative of this type of active agent.

RELATED APPLICATIONS

The microspheres produced herein are useful in making tablets and other dosage forms. See U.S. Applications Ser. No. 08/946,065, filed Oct. 7, 1997, entitled "Dosage Forms having Improved Release Properties" and 08/946,069, filed Oct. 7, 1997, entitled "Improved Dosage Units", both filed on the same date as this application.

BACKGROUND OF THE INVENTION

Melt-blended formulations containing active agents and solubilizers exist in the art.

U.S. Pat. No. 4,944,949 discloses micelles of non-steroidal anti-inflammatory drugs (NSAIDS) with nonionic surfactants such as poloxamers (col. 5, line 31). Micelles are aggregates in which surfactant molecules are arranged in a spheroidal structure, with the hydrophobic regions at the core and the hydrophilic regions at the other surfaces. Drug:surfactant ratios of 1:5.7 to 1:50 are disclosed at column 12, line 57.

U.S. Pat. No. 5,281,420 shows tebufelone, an anti-inflammatory agent, in solid dispersions containing 15% to 75% tebufelone and 25% to 65% of a poloxamer surfactant (col. 1, lines 35–51).

U.S. Pat. No. 5,525,355 deals with laxative compositions which contain poloxamer surfactants, as stool softeners, melt-blended with stimulants. The ratio of surfactant to stimulant is 2:1 to 20:1 (col. 2, line 22+). The compositions are administered in hard gelatin capsules.

EPO Application 0 317 780, published May 31, 1989, shows quick-release and sustained-release formulations containing dihydropyridine calcium channel blockers and poloxamer surfactants. The quick release compositions contain 0.15:1 to 0.5:1 of hydroxypropylmethylcellulose to dihydropyridine/poloxamer complex (p. 6, l. 48–49). The complex contains 1:1 to 1:10 ratios of drug to surfactant (page 6, lines 25–27).

WO97/02017, published Jan. 23, 1997, discusses oral dosage forms which contain a solid dispersion of an active ingredient in a poloxamer polymer. The ratio of active agent to poloxamer is 0.1:1.0 to 10.0:1.0 (page 3, line 280.

U.S. Pat. No. 4,727,109 shows liquid preparations containing an active agent and a carrier system consisting of a hydrophilic component, a hydrophobic component and a solubilizer. The hydrophilic component may be a polyethylene glycol or a polyoxyethylene/polyoxypropylene copolymerizate. See column 2, lines 35–44.

U.S. Pat. No. 5,456,923 describes solid dispersions of drugs in polymers made by extruding the two together and pulverizing the extrudate. Polyoxyethylene/polyoxypropylene copolymers are disclosed, at column 3, lines 33–4, as plasticizers.

U.S. Pat No. 5,292,461 deals with pellets produced by spraying an active agent with a wetting agent. Polyethylene glycols are disclosed as lubricants (col. 7, l. 62) and agents which influence the release of the active ingredient (col. 8, l. 1–2). Poloxamers are recited as surface-active agents (col. 7, l. 65).

The art has not successfully blended polymeric solubilizing agents with actives to directly produce stable solid microspheres of uniform size. This invention describes such microspheres.

SUMMARY OF THE INVENTION

Fast release dosage forms include those in which $T_{MAX}$, or time to maximum plasma drug concentration, is shortened, i.e., made as short as possible. By "shorter Tmax" or "shortened Tmax" applicants refer to enhanced absorption of active agent(s) at earlier time points than would be found using conventional dosage forms. The microspheres of the invention generally release all active agent(s) therein in about 5 minutes or less.

The invention uses liquiflash processing to make shearform microspheres containing binary combinations of active agents and solubilizing agents. The microspheres are useful as is, i.e., in readily flowable sachets or capsule formats. Alternatively, the microspheres can be processed into capsules or tablets or used in other dosage forms, all of which exhibit fast release properties. Oral dosage forms are typical.

Because they are spherical, the microspheres of the invention are readily flowable, so that processing and delivery to the consumer are facilitated, regardless of the type of product in which they are used.

DETAILED DESCRIPTION OF THE INVENTION

The invention deals with microspheres made by subjecting at least one active and at least one solubilizer to liquiflash processing.

Liquiflash and flash flow techniques for making microspheres are known in the art. One process uses the apparatus disclosed in U.S. Pat. No. 5,851,421, issued Dec. 22, 1998. The liquiflash process is also described in U.S. Pat. No. 5,683,720, issued Nov. 4, 1997. The disclosures of both applications are incorporated herein by reference.

U.S. Pat. Nos. 5,445,769 and 5,458,823 show devices which can be used to make liquiflash microspheres. These disclosures are also incorporated herein by reference.

The Compositions

Compositions useful in the invention are binary feedstocks for liquiflash techniques. They contain, as the only ingredients:

(a) about 20% to about 80% of at least one active ingredient, and (b) about 80% to about 20% of at least one solubilizing agent.

The active ingredients useful herein can be selected from a large group of therapeutic agents. Respective classes include those in the following therapeutic categories: ace-inhibitors; alkaloids; antacids; analgesics; anabolic agents; anti-anginal drugs; anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics; anti-migraine agents; antinauseants; antipsychotics; antistroke agents; antithyroid preparations;

anabolic drugs; antiobesity agents; antiparasitics; antipsychotics; antipyretics; antispasmodics; antithrombotics; antitumor agents; antitussives; antiulcer agents; anti-uricemic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

Active agents which may be used in the invention include: acetaminophen; acetic acid; acetylsalicylic acid, including its buffered forms; acrivastine; albuterol and its sulfate; alcohol; alkaline phosphatase; allantoin; aloe; aluminum acetate, carbonate, chlorohydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; bromopheniramine and its maleate; buspirone; caffeine; calamine; calcium carbonate, casinate and hydroxide; camphor; captopril; cascara sagrada; castor oil; cefaclor; cefadroxil; cephalexin; centrizine and its hydrochloride; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine and its hydrochloride; cinnamedrine hydrochloride; citalopram; citric acid; clarithromycin; clemastine and its fumarate; clonidine and its hydrochloride salt; clorfibrate; cocoa butter; cod liver oil; codeine and its fumarate and phosphate; cortisone acetate; ciprofloxacin HCl; cyanocobalamin; cyclizine hydrochloride; cyproheptadine and its hyddrochloride; danthron; dexbromopheniramine maleate; dextromethorphan and its hydrohalides; diazepam; dibucaine; dichloralphenazone; diclofen and its alkali metal sales; diclofenac sodium; digoxin; dihydroergotamine and its hydrogenates/mesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fluoxetine; folic acid; fosphenytoin; 5-fluorouracil (5-FU); fluoxetine and its hydrochloride; furosemide; gabapentan; gentamicin; gemfibrozil; glipizide; glycerine; glyceryl stearate; granisetron and its hydrochloride; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its mono- and dinitrates; isoxicam; ketamine; kaolin; ketoprofen; lactic acid; lanolin; lecithin; leuprolide acetate; lidocaine and its hydrochloride salt; lifinopril; liotrix; loratadine; lovastatin; luteinizing hormore; LHRH (lutenizing hormone replacement hormone); magnesium carbonate, hydroxide, salicylate, and trisilicate; meclizine and its hyddrochloride; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methsergide and its maleate; methyl nicotinate; methyl salicylate; methyl cellulose; methsuximide; metoclopramide and its halides/hydrates; metronidazole and its hydrochloride; metoprotol tartrate; miconazole nitrate; mineral oil; minoxidil; morphine; naproxen and its alkali metal sodium salts; nifedipine; neomycin sulfate; niacin; niacinamide; nicotine; nicotinamide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine and its hydrochloride salt; phenytoin; pirmenol; piroxicam and its salts; polymicin B sulfate; potassium chloride and nitrate; prazepam; procainamide hydrochloride; procaterol; promethazine and its hydrochloride; propoxyphene and its hydrochloride and napsylate; pramiracetin; pramoxine and its hydrochloride salt; prochlorperazine and its maleate; propanolol and its hydrochloride; promethazine and its hydrochloride; propanolol; pseudoephedrine and its sulfates and hydrochorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline; terfenadine; thiethylperazine and its maleate; timolol and its maleate; thioperidone; trimetrexate; triazolam; tretinoin; tetracycline hydrochloride; tolmetin; tolnaftate; triclosan; trimethobenzamide and its hydrochloride; tripelennamine and its hydrochloride; tripolidine hydrochloride; undecylenic acid; vancomycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Mixtures and pharmaceutically acceptable salts of these and other actives can be used.

Particularly useful active agents are sparingly soluble solid agents whose dissolution and release properties are enhanced by the solubilizing agents used herein. These agents include $H_2$ antagonists, analgesics, including non-steroidal anti-inflammatory drugs (NSAIDs), anticholesterolemics, anti-allergy agents, and anti-migraine agents.

Analgesics include aspirin, acetaminophen, acetaminophen plus caffeine, and non-steroidal anti-inflammatory drugs (NSAIDS), e.g., ibuprofen.

Useful NSAIDs include ibuprofen; diclofenac and its alkali metal salts; fenoprofen and its metal salts; ketoprofen, naproxen and its alkali metal salts; and piroxicam and its salts.

$H_2$-antagonists which are contemplated for use in the present invention include cimetidine, ranitidine hydrochloride, famotidine, nizatidine, ebrotidine, mifentidine, roxatidine, pisatidine and aceroxatidine.

Useful anti-allergy agents include hydricodone and its tartrates; clemastine and its fumarate; azatadine and its maleate; acetaminophen; hydroxyzine and its pamoate and hydrochloride salts; chlorpheniramine and its maleates and tannates; pseudoephedrine and its sulfates and hydrochlorides; bromopheniramine and its maleate; dextromethorphan and its hydrohalides; loratadine; phenylephrine and its tannates and hydrochlorides; methscopolamine and its nitrates; phenylpropanolamine and its hydrochlorides; codeine and its hydrochloride; codeine and its phosphate; terfenadine; acrivastine; astemizole; cetrizine and its hydrochloride; phenindamine and its tartrate; tripelennamine and its hydrochloride; cyproheptadine and its hydrochloride; promethazine and its hydrochloride; and pyrilamine and its hydrochlorides and tannates.

Useful antimigraine agents include divalproex and its alkali metal salts; timolol and its maleate; propanolol and its hydrohalides; ergotamine and its tartrate; caffeine; sumatriptan and its succinate; dihydroergotamine, its hydrogenates/mesylates; methsergide and its maleate; isometheptene mucate; and dichloralphenazone.

Another class of drugs which can be used are antiemetics. Useful antiemetics include: meclizine and its hydrochloride; hydroxyzine and its hydrochloride and pamoate; diphenhydramine and its hydrochloride; prochlorperazine and its maleate; benzquinamide and its hydrochloride; granisetron and its hydrochloride; dronabinol; bismuth subsalicylate; promethazine and its hydrochloride; metoclopramide and its halides/hydrates; chlorpromazine; trimethobenzamide and its hydrochloride; thiethylperazine and its maleate; scopolamine; perphenazine; and ondansetron and its hydrochloride.

Other active ingredients for use in the present invention include antidiarrheals such as immodium AD, antihistamines, antitussives, decongestants, vitamins, and breath fresheners. Also contemplated for use herein are anxiolytics such as Xanax; antipsychotics such as Clozaril and Haldon; antihistamines such as Seldane, Hismanal, Relafen, and Tavist; antiemetics such as Kytril and Cesamet; bronchodilators such as Bentolin, Proventil; antidepressants such as Prozac, Zoloft, and Paxil; antimigranes such as Imigran, ACE-inhibitors such as Vasotec, Capoten and Zestril; Anti-Alzheimers agents such as Nicergoline; and $Ca^{II}$-Antagonists such as Procardia, Adalat, and Calan.

Among the anticholesterolemics, the statins, e.g., lovastatin, provastatin and the like are notable.

Combinations of various types of drugs, as well as combinations of individual drugs, are contemplated.

The solubilizing agents, or solubilizers, used herein are commercially available hydrophilic surfactants.

One group of solubilizers are diblock copolymers containing only polyoxyethylene units and polyoxypropylene units. Poloxamers containing polyoxyethylene and polyoxypropylene block segments are very useful, with those having about 60% to about 90%, and particularly those having about 70% to about 80%, polyoxyethylene units being notable. Suitable polymers are sold using "Lutrol," "Monolan" and "Pluronic" trade names (BASF manufacturer). Poloxamer 188 (Pluronic F68) is effective. This surfactant contains 80 and 27 polyoxyethylene units and has an average molecular weight of about 7680 to 9510. See Handbook of Pharmaceutical Excipients (2nd Edition), 1994, pages 352–354, the disclosure of which is hereby incorporated by reference.

Other useful "Pluronic" polymers include those designated as F87, F108 and F127 and F237.

Another group of solubilizers are polyethylene glycol esters sold as "Gelucire" (Gattefosse). "Gelucire 50/13" is a polyethylene glycol-32 glyceryl palmitostearate (HLB 13).

The solid microspheres of the invention may be coated with one or more pharmaceutical coatings. However, any coating may not significantly alter the fast release properties of the microspheres or dosage forms, e.g., tablets, in which they are used. Useful coatings include aesthetic coatings, taste-masking coatings, enteric coatings and others conventionally used in the pharmaceutical field. Coatings will be present in amounts consistent with their functions—i.e, in suitable pharmaceutical amounts.

Suitable amounts and types of pharmaceutical excipients, e.g., filters, flavors, flow control agents, lubricants, diluents and the like can be blended with the microspheres before or during the preparation of a dosage form.

TABLE 1

Tablet Ingredients

| INGREDIENT | BROAD RANGE (%) | NARROW RANGE (%) |
|---|---|---|
| MICROSPHERES | 40–80 | 53–63 |
| SOLID DILUENTS | 15–55 | 30–40 |
| DISINTEGRANT | 0.5–10 | 2–4 |
| GLIDANT | 0.2–5 | 1–3 |
| LUBRICANT | 0.2–5 | 1–3 |
| OTHER ADDITIVES | 0–10 | 0–5 |

The solid diluent is generally a bulking agent. It is typically present a weight concentration which is ½ to ⅔ of the concentration of microspheres.

Useful solid diluents are microcrystalline cellulose products having particle sizes of about 20 micrometers ($\mu$m) to about 200 micrometers. The Avicel products, especially Avicel PH101 (FMC) are effective.

Disintegrants are used to assist in the release of the active agent after the tablet has been ingested. Useful disintegrants include croscarmellose sodium, polyvinylpyr-rolidone (PVP), and sodium starch glycolate. Ac-Di-sol, a croscarmellose sodium product made by FMC, is very useful, as is Kollidon CL-M, a micronized crospovidone. Mixtures are operable.

One or more glidants such as starch, talc, lactose, stearates and colloidal silica can be used. Cab-o-sil M5, a brand of colloidal silica made by Cabot, is very useful.

Lubricants are used in the tablet compositions, among them stearic acid, adipic acid, fatty acid esters, talc, magnesium stearate, mineral oil and the like and mixtures thereof. Stearic acid powder, such as that made by Sherex Chemical Co., is highly effective.

Other conventional pharmaceutical additives can be employed. Ingredients such as colorants, flavors, taste-masking agents, flow control agents, perfumes and stabilizers can be included in minor amounts.

Optionally, the microspheres can be coated, or encapsulated, with materials which alter such properties as stability, taste, dissolution, appearance and the like. Such coatings typically contain one or more pharmaceutically acceptable polymers, e.g., cellulosics.

The Processes

Liquiflash processing involves providing the ingredients at a particle size of about 2 to about 500 microns. Grinding/milling may be necessary as preliminary steps. The particles are then blended and used as a feedstock for a suitable device wherein heat and pressure conditions are controlled to effect morphological changes in the feedstock.

Inside the device, the feedstock particles lose their resistance to liquid flow and become "liquiform." In this state, the material is physically transformed from its original solid state, through a liquid state and back to a solid state instantaneously. While the particles undergo this transformation, they are acted upon by centrifugal force, or another shearing force, which force separates them into discrete spherical particles. This is termed spheronization. They exit the device as monodispersed discretized microspheres of about 10 to about 600 microns and generally about 50 to about 300 microns particle diameter.

U.S. Pat. Nos. 5,445,769; 5,458,823; 5,683,720; and 5,851,454, set out the details of the liquiflash and flash flow spheronization processes. Their disclosures are incorporated herein by reference.

The following examples illustrate the invention:

EXAMPLE I

Ibuprofen Microspheres

Three kilograms micronized ibuprofen (IBP) and two kilograms milled Poloxamer 188 were added to a Stephan mixer in the following order: (1) one-half of the solubilizer, (2) all of the IBP, (3) the remaining portion of the solubilizer. The ingredients were mixed for about three minutes. This mixture was used as a feedstock, as follows:

The feedstock was fed to the 5-inch spinning head disclosed in U.S. Pat. No. 5,851,454, issued Dec. 22, 1998. The head speed was increased to 60 Hz while the heating elements were raised to a temperature which produced liquiflash conditions (about 60° C. to 75° C.).

The spinning head forced the material through its orifices and the product was permitted to free fall a distance of from six to eight feet below the head. It consists of spheres containing 60:40 IBP:solubilizer having a highly consistent particle size, with diameters ranging from about 100 to about 500 microns.

The solid microspheres can be used as is, e.g., in a sachet, or powder, delivery system. Alternatively, they can be used in liquid, gel, tablet or capsule forms. Solid dosage forms are very effective.

Optionally, one or more coatings, such as aesthetic coating(s), taste-masking coating(s) or enteric coating(s), can be applied before the microspheres are used to deliver active agents to individuals.

EXAMPLE II

Ibuprofen Dissolution Studies

A. 40:60 IBP/Poloxamer.

Using a procedure similar to that of Example I, microspheres containing 40% unmicronized IBP and 60% milled Poloxamer 188 were produced. These spheres were subjected to dissolution testing using USP Method II in phosphate buffer adjusted to pH 6.0 (37° C.).

The microspheres demonstrated the following dissolution properties in the pH 6 medium:

| MINUTES | PERCENT DISSOLVED |
| --- | --- |
| 5 | 92 |
| 10 | 96 |
| 20 | 96 |
| 45 | 95 |
| 60 | 95 |

B. 50:50 IBP/Poloxamer.

Using the procedure of Example I, microspheres of 50% micronized IBP and 50% milled Poloxamer 188 were made.

Using the testing method described in A, above, dissolution studies were run in pH 6.0 medium. The properties were:

| MINUTES | PERCENT DISSOLVED* |
| --- | --- |
| 5 | 102 |
| 10 | 102 |
| 20 | 102 |
| 45 | 102 |
| 60 | 101 |

*Calculated values

EXAMPLE III

Ibuprofen Microsphere Studies

In bioavailability tests, microspheres containing 200 mg IBP and made in accordance with Example I gave faster times to maximum plasma concentration ($T_{max}$) than times obtained using a commercial IBP tablet (NUPRIN, Bristol-Myers Squibb Co.).

The tests were designed to determine IBP plasma concentrations at various points in time. Enhanced absorption of ibuprofen was seen at earlier time points, with individual subject plasma concentration time profiles given below. $T_{max}$ was determined from the concentration data, and was found to be 1.10 hours for the microspheres and 1.38 hours for the commercial product.

Ten healthy male volunteers took paret in a single dose, randomized crossover study. Plasma samples were collected pre dose and at 0.25, 0.5, 0.75, 1, 1,25, 1,5, 1,75, 2, 2.25, 2.5, 3, 4, 6, 8, 10 and 12 hours post-dose.

The following tables show individual subject plasma concentration-time profiles at early time points comparing fast release microspheres and NUPRIN.

| Subject | 0.25 hours | 0.5 hours |
| --- | --- | --- |
| A. Micropheres of the Invention | | |
| 1 | 0 | 15.4 |
| 2 | 0 | 7.31 |
| 3 | 0.418 | 7.31 |
| 4 | 3.53 | 9.88 |
| 5 | 8.74 | 22.2 |
| 6 | 0.250 | 2.34 |
| 7 | 2.73 | 5.63 |
| 8 | 0.29 | 4.43 |
| 9 | 3.65 | 8 |
| 10 | 1.78 | 10.8 |

-continued

| Subject | 0.25 hours | 0.5 hours |
|---|---|---|
| Average | 2.1397 | 9.33 |
| SD | 2.735264 | 5.787295 |
| B. NUPRIN | | |
| 1 | 10.4 | 14.5 |
| 2 | 9.24 | 13 |
| 3 | 7.64 | 11.5 |
| 4 | 5.82 | 9.28 |
| 5 | 6.65 | 14.5 |
| 6 | 6.09 | 11.8 |
| 7 | 6.15 | 11.8 |
| 8 | 0.914 | 6.2 |
| 9 | 10.3 | 20 |
| 10 | 16.7 | 19.9 |
| Average | 7.9904 | 13.248 |
| SD | 4.113166 | 4.290661 |

EXAMPLE IV

Ibuprofen Tablets

Rapidly disintegrating tablets were prepared containing 58% of 60:40 ibuprofen:Pluronic F-68; 35% Avicel PH101; 3% croscarmellose sodium; 2% Cab-o-sil and 2% Stearic acid. The ingredients were blended in a V-blender and compressed on a Killian T200 rotary tablet press using 8×16 mm caplet tooling.

EXAMPLE V

Ibuprofen Tablet Dissolution Studies

Rapidly disintegrating tablets containing 60:40 ibuprofen:solubilizer subjected to dissolution testing using USP Method II, 50 rpm), phosphate buffer (900 mL, 37° C.) adjusted to pH 5.2. They had the following dissolution profile:

| TIME (MINUTES) | PERCENT DISSOLVED |
|---|---|
| 5 | 77 |
| 10 | 86 |
| 20 | 89 |
| 30 | 91 |
| 45 | 92 |
| 60 | 92 |

For comparison, a dissolution study was run on 200 mg tablets of ADVIL, a commercially available preparation of Whitehall Labs (American Home Products Corp.).

Each tablet is believed to contain: ibuprofen, acetylated monoglyceride, beeswax and/or carnauba wax, croscarmellose sodium, iron oxides, lecithin, methylparaben, microcrystalline cellulose, pharmaceutical glaze, povidone, propylparaben, silicon dioxide, simethicone, sodium benzoate, sodium lauryl sulfate, starch, stearic acid, sucrose, and titanium dioxide. See page 870 of the *Physician's Desk Reference for Non-prescription Drugs*, 16th ed. (1995).

Using the same conditions as above, the ADVIL tablets had the following dissolution profile:

| TIME (MINUTES) | PERCENT DISSOLVED |
|---|---|
| 5 | 23 |
| 15 | 37 |
| 30 | 48 |
| 45 | 54 |
| 60 | 58 |

Clearly, the microspheres in the tablets of the invention dissolved faster than the commercial formulation. Seventy-seven percent (77%) of the ibuprofen in the microspheres was dissolved in 5 minutes, compared to 23% dissolution of ADVIL in the same time period.

Reasonable variations, such as those which would occur to a skilled artisan, can be made herein without departing from the scope of the invention.

We claim:

1. Microparticles useful in making dosage forms having improved dissolution and shorter time to maximum plasma concentration ($T_{max}$) consisting essentially of
   (a) about 20% to about 80% of one or more analgesic agents, and
   (b) about 80% to about 20% of one or more polymeric solubilizing agents, wherein (b) is at least one diblock copolymer containing polyoxyethylene and polyoxypropylene units.

2. The microparticles of claim 1 wherein the analgesic is ibuprofen.

3. The microparticles of claim 2, wherein the ratio of (a) to (b) is about 40:60.

4. The microparticles of claim 2, wherein the ratio of (a) to (b) is about 50:50.

5. The microparticles of claim 2, wherein the ratio of (a) to (b) is about 60:40.

6. A dosage unit comprising the microparticles of claim 1, further comprising one or more pharmaceutically acceptable excipients.

7. The dosage unit of claim 6 wherein the one or more analgesic agents is ibuprofen.

8. The dosage unit of claim 7 wherein all active agent(s) therein are released in about 5 minutes or less.

9. The dosage unit of claim 6 which is a rapidly dissolving tablet or capsule.

10. The dosage unit of claim 9 which is a tablet containing ibuprofen and a solublilizer wherein the ratio of ibuprofen to solubilizer is about 60:40.

11. A process for improving dissolution and shortening the $T_{max}$ of ibuprofen, whereby all of the active agent is released in about 5 minutes or less, comprising the step of delivering ibuprofen using the tablet of claim 10.

12. A process for improving dissolution properties and shortening the $T_{max}$ of an analgesic agent comprising the step of delivering that agent using the dosage unit of claim 7.

13. The microparticles of claim 1 made by way of liquiflash processing.

14. The microparticles of claim 2 made by way of liquiflash processing.

15. The dosage unit of claim 6 wherein the microparticles are made by way of liquiflash processing.

16. The dosage unit of claim 7 wherein the microparticles are made by way of liquiflash processing.

17. The microparticles of claim 1, wherein the at least one diblock copolymer contains from about 60% to about 90% polyoxyethylene units.

18. The microparticles of claim 1, wherein the at least one diblock copolymer contains from about 70% to about 80% polyoxyethylene units.

19. The microparticles of claim 1, wherein at least one of the diblock copolymers is Polaxamer 188 (Pluronic F68).

20. The particles of claim 1, wherein one or more of the diblock copolymers is chosen from the group consisting of poloxamer 188, poloxamer 237, poloxamer 338 and poloxamer 407.

* * * * *